(12) United States Patent
Yang et al.

(10) Patent No.: US 11,696,879 B2
(45) Date of Patent: Jul. 11, 2023

(54) THERAPEUTIC DENTAL PASTES AND RELATED METHODS AND KITS

(71) Applicant: 3M INNOVATIVE PROPERTIES COMPANY, St. Paul, MN (US)

(72) Inventors: Jie Yang, Woodbury, MN (US); Richard P. Rusin, Woodbury, MN (US); Petra L. Kohler Riedi, Minneapolis, MN (US); Joel D. Oxman, Minneapolis, MN (US); Jodi L. Connell, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1263 days.

(21) Appl. No.: 16/302,394

(22) PCT Filed: May 22, 2017

(86) PCT No.: PCT/US2017/033721
§ 371 (c)(1),
(2) Date: Nov. 16, 2018

(87) PCT Pub. No.: WO2017/205230
PCT Pub. Date: Nov. 30, 2017

(65) Prior Publication Data
US 2019/0282471 A1    Sep. 19, 2019

Related U.S. Application Data

(60) Provisional application No. 62/341,933, filed on May 26, 2016.

(51) Int. Cl.
*A61K 8/25* (2006.01)
*A61K 8/24* (2006.01)
*A61K 8/41* (2006.01)
*A61K 8/42* (2006.01)
*A61K 8/44* (2006.01)
*A61Q 11/00* (2006.01)

(52) U.S. Cl.
CPC .................. *A61K 8/25* (2013.01); *A61K 8/24* (2013.01); *A61K 8/41* (2013.01); *A61K 8/42* (2013.01); *A61K 8/44* (2013.01); *A61Q 11/00* (2013.01); *A61K 2800/87* (2013.01); *A61K 2800/88* (2013.01)

(58) Field of Classification Search
CPC ............. A61K 8/41; A61K 8/42; A61Q 11/00
See application file for complete search history.

(56) References Cited

U.S. PATENT DOCUMENTS

| | | |
|---|---|---|
| 3,538,230 A | 11/1970 | Pader |
| 3,862,307 A | 1/1975 | DiGiulio |
| 4,043,327 A | 8/1977 | Potter |
| 4,209,434 A | 6/1980 | Wilson |
| 4,301,141 A | 11/1981 | Scheller |
| 4,340,583 A | 7/1982 | Wason |
| 4,894,220 A | 1/1990 | Nabi |
| 5,015,628 A | 5/1991 | Reynolds |
| 5,037,639 A | 8/1991 | Tung |
| 5,063,257 A | 11/1991 | Akahane |
| 5,266,304 A | 11/1993 | Baffelli |
| 5,589,160 A | 12/1996 | Rice |
| 5,603,920 A | 2/1997 | Rice |
| 5,616,746 A | 4/1997 | Mahieu |
| 5,624,906 A | 4/1997 | Vermeer |
| 5,651,958 A | 7/1997 | Rice |
| 5,651,959 A | 7/1997 | Hill |
| 5,658,553 A | 8/1997 | Rice |
| 5,711,936 A | 1/1998 | Hill |
| 5,716,601 A | 2/1998 | Rice |
| 5,735,942 A | 4/1998 | Litkowski |
| 5,993,784 A | 11/1999 | Hill |
| 6,001,376 A | 12/1999 | Mahieu |
| 6,174,515 B1 | 1/2001 | Suhonen |
| 6,379,654 B1 | 4/2002 | Gebreselassie |
| 6,576,225 B1 | 6/2003 | Kilcher |
| 6,669,929 B1 | 12/2003 | Boyd |
| 6,709,744 B1 | 3/2004 | Day |
| 6,780,844 B1 | 8/2004 | Reynolds |
| 8,278,368 B2 | 10/2012 | Rusin |
| 8,556,553 B2 | 10/2013 | Karlinsey |
| 8,609,071 B2 | 12/2013 | Reynolds |
| 8,647,608 B2 | 2/2014 | Yang |
| 8,710,114 B2 | 4/2014 | Rusin |
| 8,790,707 B2 | 7/2014 | Rusin |
| 8,858,921 B2 | 10/2014 | Schmid |
| 8,968,709 B2 | 3/2015 | Yang |
| 9,023,373 B2 | 5/2015 | Karlinsey |
| 9,149,661 B2 | 10/2015 | Pilch |
| 9,205,036 B2 | 12/2015 | Karlinsey |
| 9,220,673 B2 | 12/2015 | Rusin |
| 9,241,883 B2 | 1/2016 | Reynolds |
| 9,636,284 B2 | 5/2017 | Vierling |
| 2009/0186079 A1 | 7/2009 | Nichols |
| 2009/0208909 A1 | 8/2009 | Rusin |
| 2010/0150847 A1* | 6/2010 | Yang .................. A61K 8/41 564/507 |
| 2015/0125823 A1 | 5/2015 | Rusin |

FOREIGN PATENT DOCUMENTS

| | | |
|---|---|---|
| DE | 4406745 | 9/1995 |
| WO | WO 94-24097 | 10/1994 |
| WO | WO 1995-023582 | 9/1995 |
| WO | WO 2008-033911 | 3/2008 |
| WO | WO 2009-014907 | 1/2009 |

OTHER PUBLICATIONS

Newby, C.S. et al. "Benefits of a silica-based fluoride toothpaste containing o-cymen-5-ol, zinc chloride and sodium fluoride" International Dental Journal 2011; 61 (Suppl. 3): 74-80 (Year: 2011).*
Dulbecco, "Plaque formation and isolation of pure lines with poliomyelitis viruses", J. Exp. Med, 1954, pp. 167- 182.
International Search report for PCT International Application No. PCT/US2017/033721 dated Jun. 31, 2017, 5 pages.

\* cited by examiner

*Primary Examiner* — Andrew S Rosenthal

(57) ABSTRACT

Dental pastes are provided which include: (i) a compound of Formula (I), (ii) a compound of Formula (II) or a pharmaceutically acceptable salt thereof, and (iii) a dental abrasive.

17 Claims, No Drawings

THERAPEUTIC DENTAL PASTES AND RELATED METHODS AND KITS

FIELD

The present disclosure generally relates to therapeutic dental pastes, and more specifically, to dental pastes and associated methods and kits to inhibit biofilm formation in the oral cavity of a subject.

BACKGROUND

Dental plaque, which may include bacteria such as *Streptococcus mutans*, comprises a biofilm that forms on surfaces in the oral cavity. Dental plaque is at least partly responsible for dental caries, gingivitis, and periodontal diseases. Bacteria in dental plaque metabolize carbohydrates (for example, simple sugars) in the mouth and produce acids that can etch tooth enamel. The dentin thus exposed can then be colonized by bacteria. Dental plaque can serve as a substrate for the deposition of tartar or calculus. Build-up of calculus can lead to gingivitis and, ultimately, to periodontal disease. A currently available method to remove dental plaque from teeth is mechanical removal with, for example, dental floss or a toothbrush. A toothbrush can aid in removing dental plaque from exposed surfaces of a tooth, and dental floss can aid in removing dental plaque from, for example, interproximal and subgingival surfaces. Proper and regular use of dental floss and a toothbrush can mechanically remove or reduce dental plaque, and can reduce the incidence of dental caries, gingivitis, and periodontal disease. Regular visits to a dentist or hygienist to receive professional prophylaxis can also help to reduce such oral maladies. Certain antimicrobial formulations are available (in the form of mouthwashes, rinses, and toothpastes, for example) to aid in the control and treatment of dental plaque, dental caries, gingivitis, and periodontal disease. Therapeutic dental compositions and related methods to inhibit biofilm formation have been described in U.S. Pat. No. 8,968,709 (Yang et al.).

SUMMARY

As noted above, proper and regular use of dental floss and a toothbrush, as well as regular professional teeth cleaning can reduce dental plaque and the incidence of dental caries. However, dental floss and a toothbrush are not always used properly and regularly. As a result, alternative methods to control or prevent dental plaque, rather than to remove it, are desirable. Thus, that there is a need for compositions, methods, and kits to inhibit the formation of biofilms, particularly in the oral cavity.

In one aspect, the present disclosure provides a dental paste. The dental paste includes: (i) a compound of Formula I:

wherein $R^1$ is a hydrogen atom or an alkyl group, $R^2$ is $C(O)R^3$, wherein $R^3$ is a $C_7$-$C_9$ alkyl group, and n is an integer from about 2 to about 5; (ii) a compound of Formula II or a pharmaceutically acceptable salt thereof:

wherein $R^4$ is a hydrogen atom or an alkyl group, m is an integer from about 2 to about 5; and (iii) a dental abrasive.

In another aspect, a method of treating a surface in the oral cavity of a subject is provided. The method can include: (a) providing the dental paste; and (b) applying the dental paste to a surface in the oral cavity of the subject.

In another aspect, a kit for treating a surface in the oral cavity of a subject is provided. The kit can include: (a) the dental paste; and (b) an applicator.

In another aspect, a method of inhibiting biofilm formation on a surface in the oral cavity of a subject is provided. The method can include: (a) providing the dental paste; and (b) applying the dental paste to a surface in the oral cavity of the subject.

Other features and aspects of the present disclosure will become apparent by consideration of the detailed description.

DETAILED DESCRIPTION

Definitions

Any recitation of numerical ranges by end points includes all numbers subsumed within that range (e.g., 1 to 5 includes 1, 1.5, 2, 2.75, 3, 3.80, 4, 5, etc.).

The term "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

The term "paste" refers to a substance that behaves as a solid until a sufficiently large load or stress is applied, at which point it flows like a liquid. Pastes can include a suspension of a solid in a background fluid or carrier. Pastes can be classified by their viscosity or their consistency.

The term "dental paste" refers to a paste that is used in the oral cavity of a subject.

The term "toothpaste" refers to a type of dental paste used as a cleaning agent for regular individual care, such as through daily tooth brushing. Toothpastes can be used as a prophylactic measure against caries, gingivitis, or periodontitis.

The term "prophylaxis paste" (or more simply, "prophy paste") refers to a type of a dental paste used by a dental professional, such as a dentist or dental hygienist, to remove adherent deposits such as stain, plaque, or tartar which can stick to a hard surface in the oral cavity of a subject. Such adherent deposits may not be fully removed in the course of regular tooth brushing. A prophy paste can be used on a rotating prophy paste holder referred to as a "prophylaxis cup" (or more simply, "prophy cup"). Prophy pastes can also be applied with a brush, such as a rotating brush. Commercially available prophy pastes can have a different viscosity in comparison to commercially available toothpastes.

The term "therapeutic" refers to preventing, ameliorating, treating, improving, or curing a disease or condition.

The term "biofilm" refers to a matrix including bacteria. Along with bacteria, a biofilm in the oral cavity of a subject can further include epithelial cells, leukocytes, macrophages, and other oral exudate.

The term "biofilm inhibiting" refers to limiting the formation or growth of a biofilm.

The term "hard surface" refers to a surface in the oral cavity of a subject, including hard material, such as bone, dental enamel, dentin, and dental restorations.

The term "dental restorations" refers to fillings, inlays, onlays, veneers, temporary and permanent crowns or bridges, implants, or orthodontic devices and appliances such as brackets or archwires.

The term "alkyl" refers to a monovalent group that is a radical of an alkane, which is a saturated hydrocarbon. The alkyl group can be linear, branched, cyclic, or combinations thereof and can have 1 to 20 carbon atoms. In some embodiments, the alkyl group includes 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The terms "room temperature" and "ambient temperature" are used interchangeably to mean a temperature in the range of 20° C. to 25° C.

According to one aspect, the present disclosure provides a dental paste. The dental paste includes: (i) a compound of Formula I:

$$\text{HOCH}_2\text{---(CHOH)}_n\text{---CH}_2\text{NR}^1\text{R}^2,\qquad\text{I}$$

wherein $R^1$ is a hydrogen atom or an alkyl group, $R^2$ is $C(O)R^3$, wherein $R^3$ is a $C_7$-$C_9$ alkyl group, and n is an integer from about 2 to about 5; (ii) a compound of Formula II or a pharmaceutically acceptable salt thereof:

$$\text{HOCH}_2\text{---(CHOH)}_m\text{---CH}_2\text{NHR}^4\qquad\text{II}$$

wherein $R^4$ is a hydrogen atom or an alkyl group, m is an integer from about 2 to about 5; and (iii) a dental abrasive.

Dental pastes of the present disclosure include a compound of Formula I. In the compound of Formula I, the group $R^1$ is a hydrogen atom or an alkyl group. When $R^1$ is an alkyl group, the alkyl group can include about one carbon atom (i.e., $C_1$), about two carbon atoms (i.e., $C_2$), about three carbon atoms (i.e., $C_3$), about four carbon atoms (i.e., $C_4$), about five carbon atoms (i.e., $C_5$), about six carbon atoms (i.e., $C_6$), about eight carbon atoms (i.e., $C_8$), about ten carbon atoms (i.e., $C_{10}$), about twelve carbon atoms (i.e., $C_{12}$), more than about twelve carbon atoms, or a range between and including any two of these values. For example, when $R^1$ is an alkyl group, $R^1$ can be a $C_1$-$C_{12}$ alkyl group, a $C_1$-$C_{10}$ alkyl group, $C_1$-$C_6$ alkyl group, or a $C_2$-$C_7$ alkyl group. In particular embodiments, $R^1$ is a hydrogen atom or a $C_1$-$C_2$ alkyl group. When $R^1$ is an alkyl group, the alkyl group can include a straight chain alkyl group, a branched alkyl group, or a cyclic alkyl group. Non-limiting examples of alkyl groups include methyl, ethyl, 1-propyl, isopropyl, butyl, isobutyl, sec-butyl, tert-butyl, pentyl, isopentyl, neopentyl, hexyl, heptyl, 2-ethylhexyl, octyl, isooctyl, nonyl, decyl, undecyl, dodecyl, tetradecyl, pentadecyl, octadecyl, cyclohexyl, 4-methylcyclohexyl, cyclohexylmethyl, cyclopentyl, and cyclooctyl.

In the compound of Formula I, the group $R^3$ is a $C_7$-$C_9$ alkyl group, for example, an alkyl group including about seven carbon atoms (i.e., $C_7$), about eight carbon atoms (i.e., $C_8$), or about nine carbon atoms (i.e., $C_9$). Such alkyl groups can include a straight chain alkyl group, a branched alkyl group, or a cyclic alkyl group. Non-limiting examples of $C_7$-$C_9$ alkyl groups for $R^3$ include those listed for $R^1$ (e.g., heptyl, 2-ethylhexyl, octyl, isooctyl, and nonyl). In particular embodiments, $R^3$ is a $C_8$ alkyl group (e.g., octyl). It is understood that where $R^1$ is an alkyl group (rather than a hydrogen atom), such alkyl group can be the same or different from the $C_7$-$C_9$ alkyl group of $R^3$.

In the compound of Formula I, n is an integer from about 2 to about 5. In some embodiments, n is an integer having a value of about 2, about 3, about 4, or about 5. In particular embodiments, n is an integer having a value of about 4. It is understood that the dental pastes of the present disclosure can include more than one compound of Formula I and that the compounds can be represented by Formula I with different integer values of n. In these embodiments, the average value of n of a compound can be a non-integer. In particular embodiments, a dental paste of the present disclosure can include only one compound of Formula I, and n is an integer having a value of 2, 3, 4, or 5.

The dental pastes of the present disclosure further include a compound of Formula II or a pharmaceutically acceptable salt thereof. In the compound of Formula II or a pharmaceutically acceptable salt thereof, $R^4$ is a hydrogen atom or an alkyl group. When $R^4$ is an alkyl group, the alkyl group can include about one carbon atom (i.e., $C_1$), about two carbon atoms (i.e., $C_2$), about three carbon atoms (i.e., $C_3$), about four carbon atoms (i.e., $C_4$), about five carbon atoms (i.e., $C_5$), about six carbon atoms (i.e., $C_6$), about eight carbon atoms (i.e., $C_8$), about ten carbon atoms (i.e., $C_{10}$), about twelve carbon atoms (i.e., $C_{12}$), more than twelve carbon atoms, or a range between and including any two of these values. For example, when $R^4$ is an alkyl group, $R^4$ can be a $C_1$-$C_{12}$ alkyl group, a $C_1$-$C_{10}$ alkyl group, a $C_1$-$C_8$ alkyl group, a $C_1$-$C_6$ alkyl group, or a $C_2$-$C_7$ alkyl group. In particular embodiments, $R^4$ is a hydrogen atom, a $C_1$-$C_{12}$ alkyl group, a $C_1$-$C_{10}$ alkyl group, or a $C_1$-$C_8$ alkyl group. When $R^1$ is an alkyl group, the alkyl group can include a straight chain alkyl group, a branched alkyl group, or a cyclic alkyl group. Non-limiting examples of alkyl groups include methyl, ethyl, 1-propyl, isopropyl, butyl, isobutyl, sec-butyl, tert-butyl, pentyl, isopentyl, neopentyl, hexyl, heptyl, 2-ethylhexyl, octyl, isooctyl, nonyl, decyl, undecyl, dodecyl, tetradecyl, pentadecyl, octadecyl, cyclohexyl, 4-methylcyclohexyl, cyclohexylmethyl, cyclopentyl, and cyclooctyl.

In the compound of Formula II, or a pharmaceutically acceptable salt thereof, m is an integer from about 2 to about 5. In some embodiments, m is an integer having a value of about 2, about 3, about 4, or about 5. In particular embodiments, m is an integer having a value of about 4. It is understood that the dental pastes of the present disclosure can include more than one compound of Formula II or pharmaceutically acceptable salt thereof and that the compounds can be represented by Formula II (or a pharmaceutically acceptable salt thereof) with different integer values of m. In these embodiments, the average value of m can be a non-integer. In particular embodiments, the dental pastes of the present disclosure include only one compound of Formula II or a pharmaceutically acceptable salt thereof, and m is an integer having a value of 2, 3, 4, or 5.

The compound of Formula II can be in the form of a pharmaceutically acceptable salt. Pharmaceutically acceptable salts include ammonium salts. Thus, in some embodiments, a dental paste of the present disclosure can include an ammonium salt. An ammonium salt can be represented as the reaction product of an acid with an amine, or as the reaction product of an amine with an alkylating agent such as, for example, iodomethane, bromoethane, or benzyl bromide. An ammonium salt includes a protonated amine compound, for example a compound of Formula II in which the nitrogen atom of the group $NHR^4$ has been protonated with an inorganic acid, an organic acid, or a combination of an inorganic acid and an organic acid. An ammonium salt also includes an alkylated amine compound, for example a compound of Formula II in which the nitrogen atom of the group $NHR^4$ has been alkylated with an alkylating agent.

An ammonium salt includes at least one counter ion that can be an inorganic anion, an organic anion, or a combination of anions. A combination of anions includes a combination of more than one inorganic anion, a combination of more than one organic anion, or a combination of an inorganic ion and an organic anion. Inorganic ions include, for example, halide (fluoride, chloride, bromide, and iodide), nitrate, sulfate, phosphate (including one or more of phosphate, hydrogen phosphate, and dihydrogen phosphate inorganic ions), tetrafluoroborate, and tetra(aryl)borates. Tetra(aryl)borates include compounds having the formula $Z_4B^-$, where Z is an aromatic group, for example a substituted or unsubstituted phenyl group. Examples of tetra(aryl)borates include, but are not limited to, tetraphenylborate, tetrakis(4-methylphenyl)borate, tetrakis(2-methylphenyl)borate, tetrakis(1,3,5-trimethylphenyl)borate, tetrakis(4-fluorophenyl)borate, tetrakis(pentafluorophenyl)borate, and tetrakis(4-trifluoromethylphenyl)borate. Organic anions include, for example, alkanoates (such as, for example, acetate, propionate, and butanoate), benzoate, fumarate, maleate, tartrate, ascorbate, benzenesulfonate, toluenesulfonate, and citrate.

In certain implementations, an ammonium salt can be formed by protonation of a compound of Formula II with an inorganic acid, an organic acid, or a combination of an inorganic acid and an organic acid. In another embodiment, an ammonium salt can be formed by alkylation of a compound of Formula II, with an alkylating agent. In yet another embodiment, an ammonium salt can be formed by an ion exchange or metathesis reaction with a previously formed ammonium salt.

In some embodiments, the compound of Formula II is in the form of a pharmaceutically acceptable salt, such as an ammonium halide salt, an ammonium phosphate salt (including one or more of an ammonium phosphate salt, an ammonium hydrogen phosphate salt, or an ammonium dihydrogen phosphate salt), or an ammonium citrate salt.

It is recognized that the compounds of Formulas I and II include chiral carbon atoms. For simplicity, in Formulas I and II, the stereochemical configuration about each of the chiral carbon atoms is not specified. It is intended that Formulas I and II, as used in this description and in the claims, represents each of the compounds having any of the possible stereochemical configurations. In some embodiments, the compounds of Formulas I and II are amino sugar alcohols and derivatives having the common names D-glucamine, N-methyl-D-glucamine, N-ethyl-D-glucamine, N-octyl-D-glucamine, and N-methyl-N-octanoyl-D-glucamine, N-methyl-N-nonanoyl-D-glucamine, N-methyl-N-decanoyl-D-glucamine.

Surprisingly, it was found that the combination of the compound of Formula I and the compound of Formula II or a pharmaceutically acceptable salt thereof, demonstrated improved efficacy in inhibiting biofilm formation on a surface, in comparison to the compound of Formula I alone. This synergistic effect is useful for the development of improved oral care compositions, such as the presently disclosed dental pastes. In particular, it has been found that at concentrations above certain thresholds, the compound of Formula I can cause sloughing of oral tissue (e.g., soft tissues such as mucosa). Thus, the present disclosure provides for oral care compositions, including dental pastes, with a reduced concentration of the compound of Formula I, while still maintaining acceptable activity in the inhibition of biofilm formation. Similarly, the addition of the compound of Formula II or a pharmaceutically acceptable salt thereof to oral care compositions such as dental pastes including the compound of Formula I, can provide for enhanced biofilm inhibition activity.

The dental pastes of the present disclosure include an amount of the compound of Formula I sufficient to inhibit formation of a biofilm. In some embodiments, the dental pastes can include an amount of the compound of Formula I sufficient to inhibit the formation of a biofilm in the oral cavity of a subject. In some embodiments, the dental pastes can include an amount of the compound of Formula I sufficient to inhibit the formation of a biofilm on a hard surface in the oral cavity of a subject. In such embodiments, the hard surface can include a tooth. In other embodiments, the dental pastes can include an amount of the compound of Formula I sufficient to inhibit the formation of a biofilm on a dental restoration. The dental paste can include about 40 wt.-% (weight percent), about 30 wt.-%, about 20 wt.-%, about 16 wt.-%, about 12 wt.-%, about 10 wt.-%, about 6 wt.-%, about 4 wt.-%, about 3.75 wt.-%, about 3.5 wt.-%, about 3.25 wt.-%, about 3 wt.-%, about 2.75 wt.-%, about 2.5 wt.-%, about 2.25 wt.-%, about 2 wt.-%, about 1.75 wt.-%, about 1.5 wt.-%, about 1.25 wt.-%, about 1 wt.-%, about 0.75 wt.-%, about 0.5 wt.-%, about 0.25 wt.-%, or a range between and including any two of these values, of the compound of Formula I, based on the total weight of the dental paste (i.e., the combined weights of the compound of Formula I, the compound of Formula II, the dental abrasive, and any other components which can be optionally included in the dental paste). In certain embodiments, the dental paste includes about 0.25 wt.-% to about 40 wt.-%, about 0.25 wt.-% to about 20 wt.-%, about 0.25 wt.-% to about 10 wt.-%, about 0.25 wt.-% to about 5 wt.-%, about 0.25 wt.-% to about 4 wt.-%, about 0.5 wt.-% to about 3.5 wt.-%, about 1 wt.-% to about 3 wt.-%, about 1.5 wt.-% to about 2.5 wt.-%, or about 2 wt.-% of the compound of Formula I, based on the total weight of the dental paste. In other embodiments, the amount of the compound of Formula I in the dental paste is at least about 0.25 wt.-%, based on the total weight of the dental paste.

In some embodiments, the dental pastes can provide a concentration of the compound of Formula I, up to about the solubility limit of the compound, in a medium such as, for example, water, culture broth, or saliva. In certain embodiments, the dental pastes can provide a concentration of the compound of Formula I, less than the solubility limit of the compound, in a medium such as, for example, water, culture broth, or saliva. It is recognized that the solubility limit can be different in different media. As used herein, the term "provide a concentration" of a compound of Formula I refers to a property of the dental pastes to release or transfer to a medium such as, for example, water, culture broth, or saliva an amount of a compound, resulting in a concentration of the compound, in the medium. In some embodiments, the dental pastes can provide a concentration of the compound of Formula I, up to about 0.5 molar, up to about 0.3 molar, up to about 0.15 molar, up to about 0.1 molar, up to about 0.05 molar, up to about 0.03 molar, up to about 0.02 molar, up to about 0.01 molar, up to about 0.005 molar, up to about 0.002 molar, or up to about 0.001 molar in a medium. In certain embodiments, the dental pastes can provide a concentration of a compound of Formula I up to about the solubility limit of the compound, in a medium.

As mentioned above, the dental pastes of the present disclosure include the compound of Formula II, or a pharmaceutically acceptable salt thereof. The dental paste can include about 40 wt.-%, about 30 wt.-%, about 20 wt.-%, about 16 wt.-%, about 12 wt.-%, about 10 wt.-%, about 6 wt.-%, about 4 wt.-%, about 3.75 wt.-%, about 3.5 wt.-%, about 3.25 wt.-%, about 3 wt.-%, about 2.75 wt.-%, about 2.5 wt.-%, about 2.25 wt.-%, about 2 wt.-%, about 1.75 wt.-%, about 1.5 wt.-%, about 1.25 wt.-%, about 1 wt.-%, about 0.75 wt.-%, about 0.5 wt.-%, about 0.25 wt.-%, or a range between and including any two of these values, of the compound of Formula II or a pharmaceutically acceptable salt thereof, based on the total weight of the dental paste. In certain embodiments, the dental paste includes about 0.25 wt.-% to about 40 wt.-%, about 0.25 wt.-% to about 20 wt.-%, about 0.25 wt.-% to about 10 wt.-%, about 0.25 wt.-% to about 5 wt.-%, about 0.25 wt.-% to about 4 wt.-%, about 0.5 wt.-% to about 3.5 wt.-%, about 1 wt.-% to about 3 wt.-%, about 1.5 wt.-% to about 2.5 wt.-%, or about 2 wt.-% of the compound of Formula II or a pharmaceutically acceptable, based on the total weight of the dental paste. In other embodiments, the amount of the compound of Formula II or the pharmaceutically acceptable salt thereof in the dental paste is at least about 0.25 wt.-%, based on the on the total weight of the dental paste.

It is understood that the amounts of the compound of Formula I and the compound of Formula II or a pharmaceutically acceptable salt thereof in the dental pastes can and may differ. For example, the dental paste can include about 2 wt.-% of the compound of Formula I and about 1 wt.-%, about 2.5 wt.-%, or 3 wt.-%, of the compound of Formula II or a pharmaceutically acceptable salt thereof, based on the total weight of the dental paste. In certain embodiments, the amounts of the compound of Formula I and the compound of Formula II or pharmaceutically acceptable salt thereof, are each, independently, about 10 wt.-%, about 6 wt.-%, about 4 wt.-%, about 3.75 wt.-%, about 3.5 wt.-%, about 3.25 wt.-%, about 3 wt.-%, about 2.75 wt.-%, about 2.5 wt.-%, about 2.25 wt.-%, about 2 wt.-%, about 1.75 wt.-%, about 1.5 wt.-%, about 1.25 wt.-%, about 1 wt.-%, about 0.75 wt.-%, about 0.5 wt.-%, about 0.25 wt.-%, or a range between and including any two of these values, based on the total weight of the dental paste. In a particular embodiment, the amounts of the compound of Formula I and the compound of Formula II are each about 2 wt.-%, based on the total weight of the dental paste.

Dental pastes of the present disclosure also include a dental abrasive. In general, the dental abrasive should be suitable for use in an oral environment. The dental abrasive type and characteristics (e.g., particle size, hardness, etc.), and the amount of dental abrasive in the dental paste, can be selected so that tooth enamel and dentin are not excessively abraded in the course of normal use of the dental paste, such as during tooth brushing or a during a prophylaxis procedure. The dental abrasive can serve one or more functions including but not limited to abrading and/or otherwise cleaning debris and/or plaque from the tooth surface, removing stains from the tooth surface, polishing the tooth surface, and/or providing a whitening effect on tooth.

Examples of suitable dental abrasives can include, but are not limited to, silica, silica gel, hydrated silica, precipitated silica, fused silica, alumina, calcined alumina, insoluble phosphates, calcium carbonate, ground glass, silicon carbide, ilmenite, sodium bicarbonate, bentonite, mica, zirconia, zirconia silicate, topaz, titanium dioxide, precipitated lime, chalk, pumice (e.g., flour of pumice), zeolites, talcum, kaolin, diatomaceous earth, silicates, glycine, resinous abrasives such as urea-formaldehyde condensation products, and the like. Among phosphates useful as dental abrasives are orthophosphates, polymetaphosphates and pyrophosphates, and salts thereof; illustrative examples are dicalcium orthophosphate dihydrate, dicalcium phosphate, calcium pyrophosphate, tricalcium phosphate, calcium polymetaphosphate, hydroxyapatite, magnesium orthophosphate, and insoluble sodium polymetaphosphate.

Also useful as a dental abrasive of the present disclosure is perlite, for example as described in U.S. Pat. No. 5,266,304 (Baffelli et al.) and U.S. Pat. No. 6,576,225 (Kilcher et al.), each of which is incorporated herein by reference in its entirety.

In some embodiments, a water-soluble dental abrasive can be used (alone or in combination with other dental abrasives, each of which can be water soluble or water insoluble), such as described in U.S. Pat. No. 8,858,921 (Schmid et al.), which is incorporated herein by reference in its entirety. In such embodiments, the dental pastes can be substantially free of water (e.g., less than about 5 wt.-% water or less than about 1 wt.-% water, based on the total weight of the dental paste), and optionally include a water miscible or water soluble liquid.

The average particle size of the dental abrasive is generally about 0.1 micrometers, about 1 micrometers, about 5 micrometers, about 10 micrometers, about 15 micrometers, about 20 micrometers, about 25 micrometers, about 30 micrometers, about 35 micrometers, about 40 micrometers, about 50 micrometers, about 75 micrometers, about 90 micrometers, about 100 micrometers, about 150 micrometers, about 200 micrometers, about 250 micrometers, about 300 micrometers, or a range between and including any two of these values. For example, in some embodiments, the average particle size of the dental abrasive is about 0.1 to about 300 micrometers, about 20 to about 300 micrometers, about 90 to about 300 micrometers, about 0.1 to about 50 micrometers, about 1 to about 40 micrometers, or about 5 to about 30 micrometers. As will be appreciated, the dental pastes of the present disclosure can include more than one dental abrasive. In such instances, the average particle size is intended to refer to the average particle size of each dental abrasive included in the dental paste. For example, a dental paste can include, as a first dental abrasive, silica with an average particle size of about 1 to about 40 micrometers and, as a second dental abrasive, calcium carbonate with an average particle size of about 30 to about 75 micrometers.

In certain implementations of the dental pastes of the present disclosure, silica-containing dental abrasives of various types are incorporated because they provide excellent dental cleaning and polishing performance without unduly abrading tooth enamel or dentin. The silica-containing dental abrasive materials described herein, as well as other dental abrasives, generally have an average particle size ranging from about 0.1 to about 30 micrometers or from about 5 to about 15 micrometers. The silica-containing dental abrasive can be precipitated silica or silica gels such as the silica xerogels described in U.S. Pat. No. 3,538,230 (Pader et al.) and U.S. Pat. No. 3,862,307 (DiGuilio), each of which is incorporated herein by reference in its entirety. Additional types of silica-containing dental abrasives useful in the dental pastes of the present disclosure are described in U.S. Pat. No. 4,340,583 (Wason), U.S. Pat. No. 5,589,160 (Rice), U.S. Pat. No. 5,603,920 (Rice), U.S. Pat. No. 5,651,958 (Rice), U.S. Pat. No. 5,658,553 (Rice), and U.S. Pat. No.

5,716,601 (Rice), each of which is incorporated herein by reference in its entirety. Suitable silica-containing dental abrasives for inclusion into the dental pastes described herein are available from: Huber Engineered Materials under the tradename ZEODENT; Grace under the tradenames SYLOID and SYLODENT; and Evonik under the tradename SIDENT.

One or more dental abrasives are present, in a total amount, of about 4 wt.-%, about 5 wt.-%, about 6 wt.-%, about 8 wt.-%, about 10 wt.-%, about 15 wt.-%, about 20 wt.-%, about 30 wt.-%, about 40 wt.-%, about 50 wt.-%, about 60 wt.-%, about 70 wt.-%, about 80 wt.-%, or a range between and including any two of these values, based on the total weight of the dental paste. In some embodiments, the dental paste includes about 4 wt.-% to about 80 wt.-% dental abrasive(s), based on the total weight of the dental paste. In other embodiments, the dental paste includes about 8 wt.-% to about 50 wt.-%, about 10 wt.-% to about 50 wt.-%, about 10 wt.-% to about 30 wt.-%, or about 5 wt.-% to about 25 wt.-% of the dental abrasive(s) based on the total weight of the dental paste.

Other Dental Paste Components

In various implementations, dental pastes of the present disclosure optionally includes one or more other components, including but not limited to, carriers, additives, adjuvants, agents, and/or modifiers. Examples of such components include, but are not limited to, an anticaries agent (e.g., a fluoride source), a desensitizing agent, an antigingivitis agent, an antiplaque agent, a rheology modifier, a buffering agent, a diluent, a solvent, a surfactant, a filler, an emulsifier, a foaming agent, a pH modifying agent, a humectant, an antimicrobial agent (e.g., an antibacterial agent), a mouthfeel agent, a texture modifier, an oil, a xerostomia relief agents (e.g., a saliva stimulating agent), an anti-halitosis agent, a breath freshening agent, a sweetener, a medicament, a therapeutic agent, an anti-inflammatory agent, a flavoring agent, a coloring agent (e.g., a pigment or a dye), a preservative, a stabilizer, a tartar control agent, carbon black, a remineralization agent, an anti-erosion agent, a decorative agent, a nutrient, an enzyme (e.g., lysozyme, oxidase, etc.), a protein (e.g., enamel matrix protein, proline-rich protein), a wax, other suitable materials, and combinations and mixtures thereof, including for example, those indicated in the categories set forth below. Various dental paste components that can be employed in dental pastes of the present disclosure can also include those disclosed in U.S. Pat. No. 5,624,906 (Vermeer), which is incorporated herein by reference in its entirety.

Any individual component of a dental paste of the present disclosure can be dissolved, dispersed, suspended, or emulsified in the dental paste. It is understood that while general attributes of each of the categories of components can differ; there can be some common attributes, and any given component can serve multiple purposes within two or more of such categories of components. For example, if sorbitol is included in the dental paste, sorbitol can act a sweetener and a humectant. It is further understood that the components of the dental pastes should be suitable for use (e.g., pharmaceutically acceptable and/or food grade) in the oral environment.

Carriers

In various embodiments, dental pastes of the present disclosure can include a carrier. The carrier, if present, can include a liquid, a solid, or both. In some embodiments, the carrier can be a liquid at about room temperature. In other embodiments, the carrier can be a solid at about room temperature. In some embodiments, the carrier can be a liquid at about the temperature of the oral cavity of a human, i.e., at about 37° C. In other embodiments, the carrier can be a solid at about the temperature of the oral cavity of a human. It is understood that a plurality of carriers can be used. Examples of liquid carriers include, but are not limited to, water, glycerin, propylene glycol, polyalkylene glycols (e.g., polyethylene glycol, polypropylene glycol, etc.), and combinations thereof.

Further examples of suitable carriers include those described in U.S. Pat. No. 6,669,929 (Boyd et al.), U.S. Pat. No. 6,379,654 (Gebreselassie et al.), and U.S. Pat. No. 4,894,220 (Nabi et al.), each of which is incorporated herein by reference in its entirety. In some embodiments, the carrier (or combinations of carriers) is substantially free of water (e.g., less than about 5 wt.-%, or less than about 1 wt.-% water, based on the total weight of the carrier(s)). In some embodiments where the carrier or combinations of carriers are substantially free of water, such carrier or combination of carriers is water miscible (e.g., water soluble). In further embodiments including carriers (or combinations of carriers) which are substantially free of water, the dental paste is also substantially free of water (e.g., less than about 5 wt.-% water or less than about 1 wt.-% water, based on the total weight of the dental paste). In other embodiments, the dental paste includes water, and water is present in an amount of at least about 10 wt.-%, at least about 20 wt.-%, at least about 30 wt.-%, at least about 40 wt.-%, or at least about 50 wt.-%, based on the total weight of the dental paste.

Each non-carrier component of the dental paste, including but not limited to the compound of Formula I, the compound of Formula II or pharmaceutically acceptable salt thereof, and the dental abrasive, can independently be dissolved, dispersed, suspended, or emulsified in the carrier. In some embodiments, at least one component of the dental paste is dissolved in the carrier. In some embodiments, at least one component of the dental paste is dispersed in the carrier. In some embodiments, at least one component of the dental paste is suspended in the carrier. In some embodiments, at least one component of the dental paste is emulsified in the carrier. In some embodiments, the compound of Formula I and the compound of Formula II or a pharmaceutically acceptable salt thereof are each dissolved in the carrier.

Fluoride Sources (Anticaries Agents)

In some embodiments, dental pastes of the present disclosure can include one or more anticaries agents, such as for example, one or more fluoride sources. Such fluoride sources release, or otherwise provide, fluoride ions in the oral cavity. The fluoride source can be an inorganic fluoride source, an organic fluoride source, or a combination thereof.

Examples of inorganic fluoride sources can include, but are not limited to, alkali metal, alkaline earth metal and ammonium salts of fluoride, such as for example potassium fluoride, sodium fluoride, ammonium bifluoride, calcium fluoride, a copper fluoride (e.g., cuprous fluoride, cupric fluoride), barium fluoride, sodium fluorosilicate, ammonium fluorosilicate, sodium fluorozirconate, sodium monofluorophosphate, aluminum mono- and di-fluorophosphate, fluorinated sodium calcium pyrophosphate, stannous fluoride, zinc fluoride, lithium fluoride, cesium fluoride, aluminum fluoride, indium fluoride, stannous fluorozirconate, ferric fluoride, nickel fluoride, palladium fluoride, silver fluoride, zirconium fluoride, silver diamine fluoride, and combinations thereof. Another class of fluoride sources is fluoride-containing glasses, such as fluoroaluminosilicate glasses. Suitable fluoroaluminosilicate glasses are described in U.S. Pat. No. 5,063,257 (Akahane et al.), U.S. Pat. No. 4,209,434 (Wilson et al.), and U.S. Pat. No. 4,043,327 (Potter et al.), each of which is incorporated herein by reference in its entirety. In some embodiments, the dental pastes include an inorganic fluoride sources such as sodium fluoride, stannous fluoride, sodium monofluorophosphate, silver diamine fluoride, strontium fluoride, calcium fluoride, fluoroaluminosilicate glass, or a combination thereof.

Organic fluoride sources can include, but are not limited to, N,N,N'-tris(2-hydroxyethyl)-N'-octadecyl-1,3-diaminopropane dihydrofluoride, hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, delta 8-9 octadecenylbenzyldimethylammonium fluoride, dioctyldiethylammonium fluoride, cyclohexylcetyldimethylammonium fluoride, furfuryllauryidimethylammonium fluoride, phenoxyethylcetyldimethylammonium fluoride, N,N'-tetramethyl-N,N'-dilaurylethylenediammonium difluoride, N-cetylpyridinium fluoride, N,N-dilaurylmorpholinium fluoride, N-myristyl-N-ethylmorpholinium fluoride, N-(octylaminocarbonylethyl)-N-benzyldimethylammonium fluoride, N—(B-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N,N'-dimethylaminocarbonyl)-ethyl]-N-dodecyidiethylammonium fluoride, N-carboxymethyl-N-cicosyldimethylammonium fluoride, olaflur (N'-octadecyltrimethylendiamine-N,N,N'-tris(2-ethanol) dihydrofluoride), betaine hydrofluoride, sarcosine stannous fluoride, alanine stannous fluoride, glycine potassium fluoride, sarcosine potassium fluoride, glycine hydrofluoride, tetrapropylammonium tetrafluoroborate, tetrabutylammonium tetrafluoroborate, benzyltriethylammonium tetrafluoroborate, lysine hydrofluoride, alanine hydrofluoride, betaine zirconium fluoride, and mixtures thereof. In some embodiments, the organic fluoride source can include tetrapropylammonium tetrafluoroborate, tetrabutylammonium tetrafluoroborate, benzyltriethylammonium tetrafluoroborate, or a combination thereof.

The fluoride source, if present, can be present in the dental pastes in an amount sufficient to release between about 200 ppm to 6,000 ppm fluoride ion, in some embodiments from about 800 to about 1,500 ppm fluoride ion or about 2,500 to about 5,000 ppm fluoride ion. In some dental pastes intended for in-office procedures, the fluoride source is present in an amount sufficient to release between about 10,000 to 23,000 ppm fluoride ion. The fluoride source can be present in the dental paste from about 0.001 wt.-% to about 5 wt.-%, based on the total weight of the dental paste. It is understood that the combination of fluoride sources can be used. The fluoride source can be dissolved, dispersed, suspended, or emulsified in the dental paste. In some embodiments wherein the dental pastes include a carrier, the fluoride source can be dissolved, dispersed, suspended, or emulsified in the carrier.

Antibacterial Agents

In some embodiments, dental pastes of the present disclosure can include one or more antibacterial agents. Examples of suitable antibacterial agents can include, but are not limited to, aldehydes (glutaraldyde, phthalaldehyde), salts of phenolics or acids, chlorhexidine or its derivatives (including acid adducts such as acetates, gluconates, chlorides, nitrates, sulfates or carbonates), and combinations thereof.

Non-limiting examples of antibacterial agents include: zinc salts, zinc oxide, tin salts, tin oxide, benzalkonium chloride, hexitidine, long chain alkyl ammonium or pyridinium salts (e.g., cetypyridinium chloride, tetradecylpyridinium chloride), essential oils (e.g., thymol), furanones, chlorhexidine and salt forms thereof (e.g., chlorhexidine gluconate), sanguinarine, triclosan, stannous chloride, stannous fluoride, octenidine, nonionic or ionic surfactants (e.g., quaternary ammonium compounds), alcohols (monomeric, polymeric, mono-alcohols, poly-alcohols), aromatic alcohols (e.g., phenol)), antimicrobial peptides (e.g., histatins), bactericins (e.g., nisin), antibiotics (e.g., tetracycline), aldehydes (e.g., glutaraldehyde) inorganic and organic acids (e.g., benzoic acid, salicylic acid, fatty acids, etc.) or their salts, derivatives of such acids such as esters (e.g., p-hydroxybenzoates or other parabens, glycerol esters of fatty acids such as lauricidin), fluoride, EDTA, silver compounds, silver nanoparticles, peroxides (e.g., hydrogen peroxide), and combinations thereof. The antibacterial agent can be dissolved, dispersed, suspended, or emulsified in the dental paste. In some embodiments wherein the dental pastes include a carrier, the antibacterial agent can be dissolved, dispersed, suspended, or emulsified in the carrier. In other embodiments, the dental pastes are free of an antibacterial agent.

Surfactants and Foaming Agents

Some embodiments of dental pastes of the present disclosure can include one or more surfactants. The surfactant can be an anionic surfactant, a cationic surfactant, a zwitterionic surfactant, a nonionic surfactant, or a combination thereof. In some cases, the surfactant can also serve as a foaming agent. Examples of suitable surfactants and foaming agents can include, but are not limited to, sodium lauryl sulfate, as well as those described in U.S. Pat. No. 6,174,515 (Suhonen) and U.S. Pat. No. 4,301,141 (Stier et al.), each of which is incorporated herein by reference in its entirety.

Thickeners

Dental pastes of the present disclosure can include one or more inorganic or a natural or synthetic thickeners or gelling agents. Optionally, one or more thickeners are present in a total amount of about 0.01 wt.-% to about 15 wt.-%, in some embodiments about 0.1 wt.-% to about 10 wt.-%, in some embodiments about 0.10 wt.-% to about 5 wt.-%, in some embodiments about 0.2 wt.-% to about 5 wt.-%, and in some embodiments about 0.2 wt.-% to about 1 wt.-%, based on the total weight of the dental paste. In some embodiments, the proportions of thickeners in the dental pastes are sufficient to form an extrudable, shape-retaining product which can be squeezed from a tube onto a toothbrush and will not fall between the bristles of the brush but rather, will substantially maintain its shape thereon. In some embodiments, the thickeners are sufficient to minimize splattering of the dental pastes, if for example a rotating polishing device (e.g., a prophy cup) is used during a polishing or cleaning procedure. In some embodiments, dental pastes of the present disclosure can include at least one thickener, useful for example to impart a desired consistency and/or mouth feel to the dental paste.

Any orally acceptable thickener can be used. Suitable thickeners or gelling agents useful in the dental pastes of the present disclosure include amorphous silica (e.g., as available from Huber Corporation under the trade designation ZEODENT 165), fumed silica, precipitated silica, colloidal silica, natural and synthetic gums and colloids, poloxamers, carbomers, also known as carboxyvinyl polymers, carrageenan, Irish moss, iota-carrageenan, cellulosic polymers such as hydroxyethylcellulose, carboxymethylcellulose (carmellose, cellulose gum) and salts thereof, e.g., carmellose sodium, natural gums such as karaya, xanthan, gum Arabic, gum tragacanth, polyvinylpyrrolidone, agar, colloidal magnesium aluminum silicate, and combinations thereof. One or more thickeners are optionally present in a total amount of about 0.01 wt.-% to about 15 wt.-%, for example about 0.1 wt.-% to about 10 wt.-% or about 0.2 wt.-% to about 5 wt.-%, based on the total weight of the dental paste. The thickener or gelling agent can be dissolved, dispersed, suspended, or emulsified in the dental paste. In some embodiments wherein the dental pastes include a carrier, the thickener or gelling agent can be dissolved, dispersed, suspended, or emulsified in the carrier.

Humectants

In some embodiments, dental pastes of the present disclosure can include a humectant or a plurality of humectants. Examples of humectants include, but are not limited to, polyhydric alcohols such as glycerin, sorbitol, xylitol, alkylene glycols (e.g., polyethylene glycol, propylene glycol), and combinations thereof. In various embodiments, humectants are operable to prevent hardening of the dental pastes upon exposure to air. In various embodiments humectants can also function as sweeteners. One or more humectants are optionally present, in a total amount, of about 1 wt.-%, about 2 wt.-%, about 5 wt.-%, about 10 wt.-%, about 15 wt.-%, about 20 wt.-%, about 25 wt.-%, about 30 wt.-%, about 40 wt.-%, about 50 wt.-%, about 60 wt.-%, about 70 wt.-%, about 80 wt.-%, greater than about 80 wt.-%, or at a range between and including any two of these values. For example, the dental pastes can include about 1 wt.-% to about 80 wt.-%, about 2 wt.-% to about 25 wt.-%, or about 5 wt.-% to about 15 wt.-%, based on the total weight of the dental paste. In some embodiments, the dental pastes include a humectant in an amount of at least about 10 wt.-%, at least about 15 wt.-%, or at least about 20 wt.-%, based on the total weight of the dental paste. In some such embodiments, the humectant includes sorbitol. The humectant can be dissolved, dispersed, suspended, or emulsified in the dental paste. In some embodiments wherein the dental pastes include a carrier, the humectant can be dissolved, dispersed, suspended, or emulsified in the carrier.

Buffering Agents

In some embodiments, dental pastes of the present disclosure can include a buffering agent or a buffering system, or a plurality of buffering agents or systems. Examples of suitable buffering agents include phosphate buffers as further described in U.S. Pat. No. 9,149,661 (Pilch et al.), which is incorporated herein by reference in its entirety. The buffering agent or buffering system can be dissolved, dispersed, suspended, or emulsified in the dental paste. In some embodiments wherein the dental pastes include a carrier, the buffering agent or buffering system can be dissolved, dispersed, suspended, or emulsified in the carrier.

Coloring Agents

In some embodiments, dental pastes of the present disclosure can include a coloring agent or a plurality of coloring agents. The coloring agent can be any dye or pigment. The coloring agent can be dissolved, dispersed, suspended, or emulsified in the dental paste. In some embodiments wherein the dental pastes include a carrier, the coloring agent can be dissolved, dispersed, suspended, or emulsified in the carrier.

Flavoring Agents

In some embodiments, dental pastes of the present disclosure can include a flavoring agent or a plurality of flavoring agents. In some embodiments, the flavoring agent includes an agent that imparts a flavor, e.g., a mint flavor, to the dental paste. Examples of suitable flavoring agents include, but are not limited to, oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl para-tert-butylphenylacetate, and mixtures thereof. In some embodiments, the dental pastes include an agent that imparts a tactile sensation, e.g., a cooling sensation, to the dental paste. Examples of agents which provide a cooling sensation include, but are not limited to, paramenthane carboxyamide agents such as N-ethyl-p-menthan-3-carboxamide (known commercially as "WS-3"). The flavoring agent and/or the agent which imparts a tactile sensation can each independently be dissolved, dispersed, suspended, or emulsified in the dental paste. In some embodiments wherein the dental pastes include a carrier, the flavoring agent or the agent which imparts a tactile sensation can each independently be dissolved, dispersed, suspended, or emulsified in the carrier. The dental paste can include from about 0.001 wt.-% to about 5 wt.-% of the flavoring agent (or the agent which imparts a tactile sensation), based on the total weight of the dental paste.

Sweeteners

In some embodiments, dental pastes of the present disclosure can include a sweetener or a plurality of sweeteners. Non-limiting examples of suitable sweeteners include monosaccharides, disaccharides and polysaccharides such as xylose, ribose, glucose (dextrose), mannose, galactose, maltose; sugar alcohols including erythritol, threitol, arabitol, xylitol, ribitol, mannitol, sorbitol, and the like; artificial sweeteners such as the soluble saccharin salts, i.e., sodium or calcium saccharin salts, cyclamate salts, dipeptide based sweeteners, such a L-aspartic acid derived sweeteners, such as L-aspartyl-L-phenylalanine methyl ester (aspartame), sucralose, acesulfame potassium, Advantame™, Neotame™; natural sweeteners such as stevia, thaumatin, monellin, brazzein, pentadin; and combinations thereof. The sweetener can be dissolved, dispersed, suspended, or emulsified in the dental paste. In some embodiments wherein the dental pastes include a carrier, the sweetener can be dissolved, dispersed, suspended, or emulsified in the carrier.

Remineralizing Agents

In some embodiments, dental pastes of the present disclosure can include a remineralization agent or a plurality of remineralization agents. The remineralization agent can provide for the release of calcium (e.g., calcium ions) and/or phosphorus (e.g., phosphate ions), into the oral environment to enhance remineralization, such as for example the remineralization of enamel and/or dentin. The release of calcium and phosphorus ions into the oral environment is known to enhance the natural remineralizing capability of dental structures. Suitable remineralization agents include, but are not limited to: surface treated calcium phosphate particles described in U.S. Pat. No. 8,556,553 (Karlinsey), U.S. Pat. No. 9,023,373 (Karlinsey), U.S. Pat. No. 8,790,707 (Rusin et al.), and U.S. Pat. No. 9,220,673 (Rusin et al.); particles with phosphorus-containing surface treatment described in U.S. Pat. No. 8,710,114 (Rusin et al.); and beta tricalcium phosphate as described in U.S. Pat. No. 9,205,036 (Karlinsey), each of which is incorporated herein by reference in its entirety. Also useful are compounds and methods as described in U.S. Pat. No. 5,037,639 (Tung), U.S. Pat. No. 5,993,784 (Hill), U.S. Pat. No. 5,711,936 (Hill), and U.S. Pat. No. 5,651,959 (Hill et al.), each of which is incorporated herein by reference in its entirety. Also useful are various forms of calcium phosphate particulates or nanoparticles including calcium metaphosphate, monocalcium phosphate, (anhydrous, monohydrate, or dihydrate), calcium hypophosphate, dicalcium phosphate (anhydrous, monohydrate, or dihydrate), calcium monofluorophosphate, calcium pyrophosphate, octocalcium phosphate, amorphous calcium phosphate, tricalcium phosphate (alpha or beta), hydroxyapatite, fluoroapatite, tetracalcium phosphate, and combinations thereof. Also useful are molecules with calcium and phosphorous including calcium glycerophosphate, phytin, casein and its derivatives, and the like, as described in U.S. Pat. Appl. Pub. No. 2009/0208909 (Rusin et al.) and U.S. Pat. No. 8,278,368 (Rusin et al.), U.S. Pat. No. 5,015,628 (Reynolds), U.S. Pat. No. 6,780,844 (Reynolds), U.S. Pat. No. 8,609,071 (Reynolds), and U.S. Pat. No. 9,241,883 (Reynolds), each of which is incorporated herein by reference in its entirety. Also useful are calcium phosphorous glasses as described in U.S. Pat. Appl. Pub. No. 2015/0125823 (Rusin et al.) and U.S. Pat. No. 6,709,744 (Day et al.) and U.S. Pat. No. 5,735,942 (Litowski et al.). Suitable bioactive glasses for inclusion into the dental pastes of the present disclosure are also available from Schott under the tradename VITRYXX. The remineralization agent can be dissolved, dispersed, suspended, or emulsified in the dental paste. In some embodiments wherein the dental pastes includes a carrier, the remineralization agent can be dissolved, dispersed, suspended, or emulsified in the carrier.

Desensitizing Agents

In some embodiments, dental pastes of the present disclosure can include a desensitizing agent or a plurality of desensitizing agents. The desensitizing agent can serve to combat dentin hypersensitivity. Examples of desensitizing agents include, but are not limited to, a tubule blocking agent, a nerve desensitizing agent, and combinations thereof. Examples of desensitizing agents further include, but are not limited to, strontium salts (e.g., strontium chloride, strontium acetate, and/or strontium nitrate), potassium salts (e.g., potassium citrate, potassium chloride, potassium bicarbonate, potassium gluconate, and/or potassium nitrate), stannous fluoride; basic amino acids in free or salt form (e.g., arginine, lysine, citrulline, ornithine, creatine, histidine, diaminobutanoic acid, and/or diaminoproprionic acid, and salts thereof), and combinations thereof. The desensitizing agent can be dissolved, dispersed, suspended, or emulsified in the dental paste. In some embodiments wherein the dental pastes include a carrier, the desensitizing agent can be dissolved, dispersed, suspended, or emulsified in the carrier.

Therapeutic Agents

In some embodiments, dental pastes of the present disclosure can include a therapeutic agent or a plurality of therapeutic agents. Such therapeutic agents can be an additive having a therapeutic property. The therapeutic property can include, for example, antiplaque activity, anticaries activity or antimicrobial (e.g., antibacterial) activity. In some embodiments, the therapeutic agent can have biofilm inhibiting or biofilm disrupting activity. The therapeutic agent can be dissolved, dispersed, suspended, or emulsified in the dental paste. In some embodiments wherein the dental pastes include a carrier, the therapeutic agent can be dissolved, dispersed, suspended, or emulsified in the carrier.

Binders

In some embodiments, dental pastes of the present disclosure can include a binder or a plurality of binders. The binder can provide a reservoir of the compound of Formula I in an oral cavity of a subject. The compound of Formula I can be released from the binder. The binder can hold the compound of Formula I on or near a surface in an oral cavity of a subject such that, for example, the surface can be exposed to the compound. The surface can be a hard surface, e.g., that which includes a tooth. The surface can be a dental restoration. Examples of suitable binders for are described in U.S. Pat. No. 8,968,709 (Yang et al.) which is incorporated herein by reference in its entirety.

The dental pastes can have a form including a solution, a dispersion, a suspension, an emulsion, a solid, a paste, a foam, or a gel. In some embodiments, the dental pastes are toothpastes. In some embodiments, the dental pastes are prophy pastes. Any component of the dental paste can be dissolved, dispersed, suspended, or emulsified in any other component of the dental paste. In some embodiments, one or more of the components are mutually soluble (i.e., miscible with each other).

In some embodiments, the dental paste is provided within a single part or phase. In other embodiments, the dental paste includes both a first and a second part that are separately maintained until they are mixed upon use. Maintaining the first and second parts separately requires only that the parts are maintained in such a way as to substantially prevent the interaction of one part of the dental paste with another part of the dental paste. A dual part dental paste can be employed where there are one or more incompatible ingredients (components) included in the dental paste. For example, if the dental paste includes two incompatible active ingredients, it can be advantageous to maintain them separately.

The dental paste can be formulated by combining a compound of Formula I, a compound of Formula II or a pharmaceutically acceptable salt thereof, and an abrasive, optionally with another component or components of the dental paste (e.g., a carrier such as a liquid carrier). Where the dental pastes include a liquid carrier, the compound of Formula I and/or the compound of Formula II or pharmaceutically acceptable salt thereof can be combined with the liquid carrier. The compounds can each independently be dissolved, dispersed, suspended, or emulsified in the liquid carrier. In some embodiments, all the components of the dental pastes are combined at about the same time.

Method and Kit

In another aspect, the present disclosure provides a method of treating a surface in the oral cavity of a subject, including the steps of (a) providing any one of the dental pastes disclosed herein, and (b) applying the dental paste to a surface in the oral cavity of a subject. The surface in the oral cavity of a subject includes, for example, a buccal surface, a gingival surface, a tooth, a dental restoration, and bone. In some embodiments, the surface is a hard surface, such as for example, the surface of a tooth (including vital surfaces such as enamel and/or dentin, but also non-vital surfaces such as the surface of a dental restoration). The dental pastes can be applied to the oral cavity of a subject by, for example, brushing (e.g., tooth brushing), polishing, swabbing, or combinations thereof. The application of the dental pastes to the surface in the oral cavity can further include polishing the surface, for example polishing the surface of a tooth. While polishing the surface can occur in the course of brushing (e.g., regular tooth brushing at home), polishing can be performed course of a dental prophylaxis procedure, such as that performed in a clinical environment by a dental professional (e.g., a dental hygienist). The subject can be a human, or the subject can be a non-human animal. Non-human animals include mammals such as canines and felines. The dental pastes of the present disclosure can serve to inhibit biofilm formation, for example inhibit biofilm formation on a surface in the oral cavity of a subject. Thus, in another aspect, the present disclosure also provides a method of treating a surface in the oral cavity of a subject, the method including the steps of (a) providing any one of the dental pastes disclosed herein, and (b) applying the dental paste to a surface in the oral cavity of a subject. The surface in the oral cavity of the subject and the manner of application of the dental paste can be any of those previously described.

In yet another aspect, the present disclosure provides a kit including (a) any one of the dental pastes disclosed herein, and (b) an applicator. The applicator can be a brush, a swab, a prophylaxis device and combinations thereof. Examples of prophylaxis devices include, but are not limited to, prophylaxis cups (i.e., "prophy cups") and prophylaxis angles ("prophy angles"). The applicator can be any size suitable for use in a given application. The kit can include more than one applicator or more than one kind of applicator (e.g., a brush and a swab). The kit can also include instructions for using the kit.

The dental pastes can be in contact with a surface in the oral cavity for a time sufficient to inhibit biofilm formation in the oral cavity. The time can be up to about one second, up to about five seconds, up to about ten seconds, up to about thirty seconds, up to about one minute, up to about two minutes, up to about five minutes, up to about ten minutes, up to about fifteen minutes, up to about thirty minutes, or up to about sixty minutes. The time can be less than about one month, less than about two weeks, less than about one week, less than about twenty-four hours, less than about twenty hours, less than about sixteen hours, less than about twelve hours, less than about ten hours, less than about eight hours, less than about six hours, less than about four hours, or less than about two hours.

The dental pastes can include an amount of a compound of Formula I sufficient to inhibit formation of a biofilm including at least one species of bacteria found in the oral cavity of a subject. In some embodiments, the subject is a human. In other embodiments, the subject is a non-human animal. The bacteria include, for example, *Streptococcus mutans* and *S. sanguis*.

The following embodiments are intended to be illustrative of the present disclosure and not limiting.

EMBODIMENTS

Embodiment 1 is a dental paste comprising:
(i) a compound of Formula I:

$$\text{HOCH}_2\text{---}(\text{CHOH})_n\text{---}\text{CH}_2\text{NR}^1\text{R}^2,\qquad \text{I}$$

wherein:
$R^1$ is a hydrogen atom or an alkyl group, and
$R^2$ is $C(O)R^3$, wherein $R^3$ is a $C_7$-$C_9$ alkyl group, and
n is an integer from about 2 to about 5;
(ii) a compound of Formula II or a pharmaceutically acceptable salt thereof:

$$\text{HOCH}_2\text{---}(\text{CHOH})_m\text{---}\text{CH}_2\text{NHR}^4,\qquad \text{II}$$

wherein:
$R^4$ is a hydrogen atom or an alkyl group, and
m is an integer from about 2 to about 5; and
(iii) a dental abrasive.

Embodiment 2 is the dental paste of embodiment 1, wherein $R^1$ is a hydrogen atom or a $C_1$-$C_2$ alkyl group.

Embodiment 3 is the dental paste of embodiment 1 or embodiment 2, wherein $R^3$ is a $C_8$ alkyl group.

Embodiment 4 is the dental paste of any one of embodiments 1-3, wherein n is 4.

Embodiment 5 is the dental paste of any one of embodiments 1-4, wherein $R^4$ is a hydrogen atom or a $C_1$-$C_{12}$ alkyl group.

Embodiment 6 is the dental paste of any one of embodiments 1-5, wherein m is 4.

Embodiment 7 is the dental paste of any one of embodiments 1-6, wherein $R^1$ is a $C_1$ alkyl group; $R^3$ is a $C_8$ alkyl group; n is 4; $R^4$ is a hydrogen atom or a $C_1$-$C_8$ alkyl group; and m is 4.

Embodiment 8 is the dental paste of any one of embodiments 1-7, wherein the dental abrasive includes at least one of silica, alumina, perlite, pumice, calcium carbonate, calcium pyrophosphate, dicalcium phosphate, tricalcium phosphate, sodium bicarbonate, glycine, and a combination thereof.

Embodiment 9 is the dental paste of any one of embodiments 1-8, further comprising a liquid carrier.

Embodiment 10 is the dental paste of embodiment 9, wherein the liquid carrier includes at least one of water, glycerin, propylene glycol, polyethylene glycol, and combinations thereof.

Embodiment 11 is the dental paste of any one of embodiments 1-10, further comprising a fluoride source, an antibacterial agent, a surfactant, a thickener, a humectant, a buffering agent, a coloring agent, a pigment, a flavoring agent, a sweetener, a remineralizing agent, a desensitizing agent, a foaming agent, a therapeutic agent, an antigingivitis agent, and combinations thereof.

Embodiment 12 is the dental paste of any one of embodiments 1-11, further comprising sorbitol in a concentration of at least 10 wt.-%, based on the total weight of the dental paste.

Embodiment 13 is the dental paste of any one of embodiments 1-12, wherein the dental paste is a toothpaste.

Embodiment 14 is the dental paste of any one of embodiments 1-13, wherein the dental paste is a prophy paste.

Embodiment 15 is a method of treating a surface in the oral cavity of a subject, the method comprising:
(a) providing the dental paste of any one of embodiments 1-14; and
(b) applying the dental paste to a surface in the oral cavity of the subject.

Embodiment 16 is the method of embodiment 15, wherein the surface is a hard surface.

Embodiment 17 is the method of embodiment 15 or embodiment 16, wherein the surface is a surface of a tooth.

Embodiment 18 is the method of any one of embodiments 15-17, wherein applying the dental paste comprises brushing, swabbing, or a combination thereof.

Embodiment 19 is a kit for treating a surface in the oral cavity of a subject, the kit comprising:
(a) the dental paste of any one of embodiments 1-14; and
(b) an applicator.

Embodiment 20 is the kit of embodiment 19, wherein the applicator is selected from a brush, a swab, and a combination thereof.

Embodiment 21 is a method of inhibiting biofilm formation on a surface in the oral cavity of a subject, the method comprising:

(a) providing the dental paste of any one of embodiments 1-14; and (b) applying the dental paste to a surface in the oral cavity of the subject.

It is to be understood that the invention is not limited in its application to the details of construction and the arrangement of components set forth in the above description. The invention is capable of other embodiments and of being practiced or of being carried out in various ways. Also, it is to be understood that the phraseology and terminology used herein is for the purpose of description and should not be regarded as limiting. It is to be further understood that other embodiments can be utilized, and structural or logical changes can be made without departing from the scope of the present disclosure.

The following examples are intended to be illustrative of the present disclosure and not limiting.

EXAMPLES

As used herein, all parts and percentages are by weight, all water is deionized water ("DI water"), and all molecular weights are average molecular weights, unless otherwise specified. Unless otherwise specified, materials can be obtained from Sigma-Aldrich, Milwaukee, Wis.

Materials

D-Glucamine is commercially available from TCI America (Portland, Oreg.). N-Methyl-D-glucamine and N-ethyl-D-glucamine are commercially available from MP Biomedicals (Solon, Ohio). N-methyl-N-nonanoyl-D-glucamine ("MEGA-9") is commercially available from EMD Chemicals, Inc. (San Diego, Calif.). N-Octyl-D-Glucamine is commercially available from Carbosynth, Inc. (San Diego, Calif.). Sorbitol (70 wt.-% aqueous solution) is commercially available from Spectrum Inc. (New Brunswick, N.J.). Glycerol is commercially available from Sigma-Aldrich (St. Louis, Mo.). Titanium dioxide (Type MT-500B) is available from Diacolor-Pope Inc. (Paterson, N.J.). Cellulose gum (food grade carboxymethyl cellulose, displaying a viscosity of ~3,000 cps for a 1 wt.-% solution), silica thickener (average particle size of 12 micrometers and an oil absorption value of 220 cc/100 g), and silica abrasive (mean particle size of 9 micrometers as determined by laser diffraction, an oil absorption value of 120 g/100 g, and a surface area of 45 m$^2$/g) are available from various commercial suppliers.

Preparation of Mucin-Containing Medium Supplemented with ~5 wt.-% Sucrose (MCM)

A 1-L stock solution of mucin-containing medium supplemented with ~5 wt.-% sucrose was prepared as follows. Lab-lemco beef extract powder (1.0 g, available from Thermo Fisher Scientific, Waltham, Mass.), yeast extract powder (2.0 g, available from Becton, Dickinson and Company, Franklin Lakes, N.J.), proteose peptone (5 g, available from Becton, Dickinson and Company, Franklin Lakes, N.J.), Mucin from porcine stomach, Type III (2.5 g, available from Sigma-Aldrich, St. Louis, Mo.), sodium chloride (0.35 g), calcium chloride dihydrate (0.2 g), and potassium chloride (0.2 g) were dissolved in DI water (800 mL). The pH was measured with a calibrated pH electrode (pH=6.9). Additional DI water (100 mL) was added and the solution autoclaved at 121° C. for 15 minutes. After cooling to room temperature, 40% (w/v) aqueous urea (1.25 mL, filter sterilized) was added, followed by 50% (w/v) aqueous sucrose (98.75 mL, autoclaved). The constituents of the MCM solution are summarized in Table 1.

TABLE 1

| Component | Amount (w/v) |
| --- | --- |
| Lab-Lemco beef extract powder | 0.1% |
| Yeast extract powder | 0.2% |
| Proteose peptone | 0.5% |
| Mucin from porcine stomach, Type III | 0.25% |
| Sodium chloride | 0.035% |
| Calcium chloride | 0.02% |
| Potassium chloride | 0.02% |
| Urea | 0.05% |
| Sucrose | ~5% |
| DI water | Balance |

Biofilm Microcosm Test Method

Composite disks (10 mm diameter×2.1 mm thickness) formed from a commercially available dental mill blank (Paradigm MZ 100, available from 3M Oral Care, St. Paul, Minn.) and polished to a final thickness of 2.0 mm with a 1000 grit finish were used as substrates for biofilm growth. Prior to use, the disks were disinfected in 75% (v/v) ethanol for 45 to 60 minutes. Disks were cleaned for reuse by shaking them in 1% aqueous sodium hydroxide to remove biofilm growth, rinsed with water, and stored in 50% aqueous ethanol.

One sterilized composite disk was placed per well in a sterile 24-well plate. A mixture of 1:4 human saliva from a single healthy donor:MCM (1.8 mL) was added to each disk-containing well. The 24-well plate was placed in an incubator at 37° C. with shaking (60 rpm) for 4 hours. The plate was removed from the incubator, the growth medium was removed, and fresh MCM (1.8 mL, no saliva) was added to each well and the plate incubated 4 hours at 37° C. with shaking. Hereafter, only MCM without saliva was used for further medium exchange.

The disks were then subjected to five treatment/growth cycles as follows. The liquid from the wells were removed via pipette. A treatment solution (1.8 mL) was added to each of the wells, and then removed from each well after 1 minute of disk exposure. Each disk was then rinsed with deionized water for 2 min, MCM (1.8 mL) added to each well, and the plate incubated for 4 hours at 37° C. For overnight storage under refrigeration, the MCM was removed and replaced with phosphate-buffered saline (PBS; also known as "Dulbecco A", described by Dulbecco & Vogt 1954, J. Exp. Med. 99, 167-182). The last medium change was performed two hours before end of the test method.

After the last treatment/growth cycle on the fourth day, the biofilms were collected with dried filter papers to determine the anhydrous biofilm mass for each disk. In particular, the disks with the grown biofilm were carefully transferred into new 24-well-plates filled with DI water (1.0 mL per well). Each disk was washed with DI water (1.0 mL) three times for 1 min with moderate shaking (ca. 400 rpm). After the washing, the disks were carefully blotted on filter paper to remove excess liquid. The biofilms were then removed from the disks by wiping the surfaces of each disk with filter paper which had been dried overnight in a microcentrifuge tube at 70° C. and weighed to determine the total weight of the dried paper and the microcentrifuge tube. Each filter paper with the wet biofilm was then placed back into the same microcentrifuge tube, dried overnight at 70° C., and biofilm mass determined by weighing the dry biofilm, paper, and microcentrifuge tube, and subtracting the initial mass of the tube and paper. The steps of the Biofilm Microcosm Test Method are summarized in the Table 2.

TABLE 2

| Day 1 | Sterilize substrate disks, place into wells |
| --- | --- |
| | Disk inoculation with human saliva/MCM mixture (4 hours at 37° C.) |
| | Remove human saliva/MCM mixture |
| | Add MCM (4 hour growth phase at 37° C.) |
| | Remove MCM and replace with PBS |
| | Refrigerate overnight |
| Days 2 and 3 | Remove PBS |
| | Add treatment solution, expose disk for 1 min, remove treatment solution, rinse disk with DI water |
| | Add MCM (4 hour growth phase at 37° C.) |
| | Remove MCM |
| | Add test formulation, expose disk for 1 min, remove treatment solution, rinse disk with DI water |
| | Add MCM (4 hour growth phase at 37° C.) |
| | Remove MCM and replace with PBS |
| | Refrigerate overnight |
| Day 4 | Remove PBS |
| | Add treatment solution, expose disk for 1 min, remove treatment solution, rinse disk with DI water |
| | Add MCM (4 hour growth phase at 37° C.) |
| | Collect biofilms and dry overnight |
| Day 5 | Weigh dried biofilms |

Toothpaste Formulations

Toothpaste formulations were prepared according to the components and amounts indicated in Table 3, mixing until the components were homogeneously dispersed.

TABLE 3

| | CE-1 | CE-2 | CE-3 | CE-4 | CE-5 | CE-6 | EX-1 | EX-2 | EX-3 | EX-4 |
| --- | --- | --- | --- | --- | --- | --- | --- | --- | --- | --- |
| Glycerin | 8.55 | 8.55 | 8.55 | 8.55 | 8.55 | 8.55 | 8.55 | 8.55 | 8.55 | 8.55 |
| Cellulose gum | 1.00 | 1.00 | 1.00 | 1.00 | 1.00 | 1.00 | 1.00 | 1.00 | 1.00 | 1.00 |
| DI water | 43.44 | 41.44 | 41.44 | 41.44 | 41.44 | 41.44 | 39.44 | 39.44 | 39.44 | 39.44 |
| Titanium dioxide | 0.70 | 0.70 | 0.70 | 0.70 | 0.70 | 0.70 | 0.70 | 0.70 | 0.70 | 0.70 |
| N-Methyl-D-glucamine | 0.00 | 0.00 | 2.00 | 0.00 | 0.00 | 0.00 | 2.00 | 0.00 | 0.00 | 0.00 |
| N-Ethyl-D-glucamine | 0.00 | 0.00 | 0.00 | 2.00 | 0.00 | 0.00 | 0.00 | 2.00 | 0.00 | 0.00 |
| D-glucamine | 0.00 | 0.00 | 0.00 | 0.00 | 2.00 | 0.00 | 0.00 | 0.00 | 2.00 | 0.00 |
| N-Octyl-D-glucamine | 0.00 | 0.00 | 0.00 | 0.00 | 0.00 | 2.00 | 0.00 | 0.00 | 0.00 | 2.00 |
| MEGA-9 | 0.00 | 2.00 | 0.00 | 0.00 | 0.00 | 0.00 | 2.00 | 2.00 | 2.00 | 2.00 |
| Sorbitol, 70% aqueous solution | 25.38 | 25.38 | 25.38 | 25.38 | 25.38 | 25.38 | 25.38 | 25.38 | 25.38 | 25.38 |
| Sodium fluoride | 0.21 | 0.21 | 0.21 | 0.21 | 0.21 | 0.21 | 0.21 | 0.21 | 0.21 | 0.21 |
| Sodium saccharin | 0.27 | 0.27 | 0.27 | 0.27 | 0.27 | 0.27 | 0.27 | 0.27 | 0.27 | 0.27 |
| Silica thickener | 6.50 | 6.50 | 6.50 | 6.50 | 6.50 | 6.50 | 6.50 | 6.50 | 6.50 | 6.50 |
| Silica abrasive | 13.95 | 13.95 | 13.95 | 13.95 | 13.95 | 13.95 | 13.95 | 13.95 | 13.95 | 13.95 |
| Total | 100.00 | 100.00 | 100.00 | 100.00 | 100.00 | 100.00 | 100.00 | 100.00 | 100.00 | 100.00 |

To prepare test (treatment) solutions for use in the Biofilm Microcosm Test Method, each of the toothpaste formulations in Table 3 were mixed with DI water (toothpaste:DI water=1:3, by weight), the resultant mixtures centrifuged, and the supernatant aqueous layers from the centrifuged mixtures were removed and used as the test solutions. In the same fashion, a test solution was prepared from a commercially available toothpaste (Colgate Total Clean Mint, Anticavity Fluoride and Antigingivitis toothpaste, including 0.30% triclosan, "Colgate") by mixing with DI water (toothpaste:DI water=1:3, by weight), centrifuging the mixture, and recovering the supernatant for testing.

Study 1

The Biofilm Microcosm Test Method was used to evaluate test solutions of toothpaste formulations CE-1, CE-2, CE-3, EX-1, and commercially available Colgate (positive control). The Biofilm Microcosm Test Method was repeated three times, with six replicates in each test. Human saliva used in the test method for Study 1 was provided by a single healthy volunteer (donor A). Biomass data are shown in Table 4.

TABLE 4

| | DI water (negative control) | Colgate | CE-1 | CE-2 | CE-3 | EX-1 |
| --- | --- | --- | --- | --- | --- | --- |
| Biomass Mean (mg) | 1.65 | 0.08 | 1.50 | 1.42 | 1.13 | 0.21 |
| Std. Dev. | 0.40 | 0.34 | 0.23 | 0.25 | 0.33 | 0.18 |
| N= | 18 | 18 | 18 | 18 | 17 | 18 |

The data in Table 4 show that toothpastes including only MEGA-9 (CE-2) or only N-methyl-D-glucamine (CE-3) display little inhibitory effect on biofilm growth, resulting in biomasses similar to the negative control (DI water) and CE-1. In contrast, a toothpaste including both MEGA-9 and N-methyl-D-glucamine (EX-1) provides for a significant inhibition in biofilm growth, similar to that of the commercially available, antibacterial-containing toothpaste, Colgate.

Study 2

The Biofilm Microcosm Test Method was used to evaluate test solutions of toothpaste formulations CE-2, CE-4, EX-2, and commercially available Colgate as a positive control. The Biofilm Microcosm Test Method was performed once, with six replicates in each test. Human saliva used in the test method for Study 2 was provided by a single healthy volunteer (donor B). Biomass data are shown in Table 5.

TABLE 5

| | DI water (negative control) | Colgate | CE-2 | CE-4 | EX-2 |
| --- | --- | --- | --- | --- | --- |
| Biomass Mean (mg) | 0.81 | 0.15 | 0.92 | 0.91 | 0.24 |
| Std. Dev. | 0.29 | 0.15 | 0.25 | 0.15 | 0.32 |
| N = | 6 | 6 | 6 | 6 | 6 |

The data in Table 5 show that toothpastes including only MEGA-9 (CE-2) or only N-ethyl-D-glucamine (CE-4) display little inhibitory effect on biofilm growth, resulting in biomasses similar to the negative control (DI water). In contrast, a toothpaste including both MEGA-9 and N-ethyl-D-glucamine (EX-2) provide for a significant inhibition in biofilm growth, similar to that of the commercially available, antibacterial-containing toothpaste, Colgate.

Study 3

The Biofilm Microcosm Test Method was used to evaluate test solutions of toothpaste formulations CE-2, CE-5, CE-6, EX-3, EX-4 and commercially available Colgate (positive control). The Biofilm Microcosm Test Method was performed once, with six replicates in each test. Human saliva used in the test method for Study 3 was provided by a single healthy volunteer (donor C). Biomass data are shown in Table 6.

TABLE 6

|  | DI water (negative control) | Colgate | CE-2 | CE-5 | CE-6 | EX-3 | EX-4 |
|---|---|---|---|---|---|---|---|
| Biomass Mean (mg) | 1.35 | 0.18 | 1.67 | 1.67 | 1.02 | 0.25 | 0.26 |
| Std. Dev. | 0.26 | 0.31 | 0.32 | 0.30 | 0.19 | 0.30 | 0.16 |
| N= | 12 | 18 | 12 | 12 | 12 | 12 | 12 |

The data in Table 7 show that toothpastes including only MEGA-9 (CE-2), or only D-glucamine (CE-5), or only N-octyl-D-glucamine (CE-6) display little inhibitory effect on biofilm growth, resulting in biomasses similar to the negative control (DI water). In contrast, toothpastes including both MEGA-9 and D-glucamine (EX-3), or including both MEGA-9 and N-octyl-D-glucamine (EX-4), both provide for a significant inhibition in biofilm growth, similar to that of the commercially available, antibacterial-containing toothpaste, Colgate.

The embodiments described above are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A dental paste comprising:
   (i) a compound of Formula I:

I wherein:
   $R^1$ is a $C_1$-$C_2$ alkyl group, and
   $R^2$ is $C(O)R^3$, wherein $R^3$ is a $C_7$-$C_9$ alkyl group, and n is 4;
   (ii) a compound of Formula II or a pharmaceutically acceptable salt thereof:

II wherein:
   $R^4$ is a hydrogen atom or a $C_1$-$C_{12}$ alkyl group, and m is 4;
   and (iii) a dental abrasive wherein the weight ratio of compound of Formula I to compound of Formula II is 1:1.

2. The dental paste of claim 1, wherein $R^3$ is a $C_8$ alkyl group.

3. The dental paste of claim 1, wherein $R^1$ is a $C_1$ alkyl group; $R^3$ is a $C_8$ alkyl group; n is 4; $R^4$ is a hydrogen atom or a $C_1$-$C_8$ alkyl group.

4. The dental paste of claim 1, wherein the dental abrasive includes at least one of silica, alumina, perlite, pumice, calcium carbonate, calcium pyrophosphate, dicalcium phosphate, tricalcium phosphate, sodium bicarbonate, glycine, and a combination thereof.

5. The dental paste of claim 1, further comprising a liquid carrier.

6. The dental paste of claim 5, wherein the liquid carrier includes at least one of water, glycerin, propylene glycol, polyethylene glycol, and combinations thereof.

7. The dental paste of claim 1, further comprising a fluoride source, an antibacterial agent, a surfactant, a thickener, a humectant, a buffering agent, a coloring agent, a pigment, a flavoring agent, a sweetener, a remineralizing agent, a desensitizing agent, a foaming agent, a therapeutic agent, an antigingivitis agent, and combinations thereof.

8. The dental paste of claim 1, further comprising sorbitol in a concentration of at least 10 wt.-%, based on the total weight of the dental paste.

9. The dental paste of claim 1, wherein the dental paste is a toothpaste.

10. The dental paste of claim 1, wherein the dental paste is a prophy paste.

11. A method of treating a surface in the oral cavity of a subject, the method comprising:
    (a) providing the dental paste of claim 1; and
    (b) applying the dental paste to a surface in the oral cavity of the subject.

12. The method of claim 11, wherein the surface is a hard surface.

13. The method of claim 11, wherein the surface is a surface of a tooth.

14. The method of claim 11, wherein applying the dental paste comprises brushing, swabbing, or a combination thereof.

15. A kit for treating a surface in the oral cavity of a subject, the kit comprising:
    (a) the dental paste of claim 1; and
    (b) an applicator.

16. The kit of claim 15, wherein the applicator is selected from a brush, a swab, and a combination thereof.

17. A method of inhibiting biofilm formation on a surface in the oral cavity of a subject, the method comprising:
    (a) providing the dental paste of claim 1; and
    (b) applying the dental paste to a surface in the oral cavity of the subject.

* * * * *

UNITED STATES PATENT AND TRADEMARK OFFICE
CERTIFICATE OF CORRECTION

PATENT NO. : 11,696,879 B2
APPLICATION NO. : 16/302394
DATED : July 11, 2023
INVENTOR(S) : Jie Yang et al.

It is certified that error appears in the above-identified patent and that said Letters Patent is hereby corrected as shown below:

In the Claims

Column 24
Line 5 (approx.), In Claim 1, delete "Formula Ito" and insert -- Formula I to --, therefor.

Signed and Sealed this
Fifth Day of December, 2023

Katherine Kelly Vidal
*Director of the United States Patent and Trademark Office*